(12) United States Patent
Sjaarda

(10) Patent No.: US 6,695,821 B1
(45) Date of Patent: Feb. 24, 2004

(54) SURGICAL INFUSION TOOL WITH FLOW DIFFUSER

(76) Inventor: Raymond N. Sjaarda, 40 Springhill Farm Ct., Hunt Valley, MD (US) 21030

( * ) Notice: Subject to any disclaimer, the term of this patent is extended or adjusted under 35 U.S.C. 154(b) by 312 days.

(21) Appl. No.: 09/098,799

(22) Filed: Jun. 17, 1998

(51) Int. Cl.[7] .............................................. A61M 25/00
(52) U.S. Cl. ...................................... 604/264; 604/294
(58) Field of Search ............................. 604/22, 27, 30, 604/48, 264, 280, 294, 295, 298

(56) References Cited

U.S. PATENT DOCUMENTS

| | | | |
|---|---|---|---|
| 671,477 A | * | 4/1901 | Graham ....................... 604/215 |
| 3,955,579 A | * | 5/1976 | Bridgman ................... 128/304 |
| 4,011,869 A | * | 3/1977 | Seiler, Jr. .................... 128/276 |
| 4,513,745 A | * | 4/1985 | Amoils ........................ 128/305 |
| 4,764,165 A | * | 8/1988 | Reimels et al. ............... 604/35 |
| 5,407,441 A | * | 4/1995 | Greenbaum ................. 604/280 |
| 5,487,725 A | | 1/1996 | Peyman |
| 5,547,473 A | | 8/1996 | Peyman |
| 5,597,381 A | | 1/1997 | Rizzo, III |
| 5,643,304 A | * | 7/1997 | Schecter et al. ............ 606/171 |
| 5,662,619 A | * | 9/1997 | Zarate ......................... 604/272 |
| 5,716,363 A | * | 2/1998 | Josephberg ................. 606/107 |
| 5,893,862 A | * | 4/1999 | Pratt et al. ................... 606/170 |
| 5,919,157 A | * | 7/1999 | Strukel ........................ 604/22 |
| 5,989,262 A | * | 11/1999 | Josephberg ................. 606/107 |

FOREIGN PATENT DOCUMENTS

| | | |
|---|---|---|
| EP | 0 271 775 A2 | 6/1988 |
| GB | 1349882 | 4/1974 |

OTHER PUBLICATIONS

Visitec catalog (4 pages attached).

* cited by examiner

*Primary Examiner*—LoAn H. Thanh
(74) *Attorney, Agent, or Firm*—Brett Trout

(57) ABSTRACT

An intraocular surgical tool for infusing fluid into an eye of a patient. The tool is provided with a housing having a longitudinal bore opening into an aperture. A flow diffuser is positioned over the aperture to diffuse and slow the flow of fluid through the aperture. The flow diffuser may be a cone positioned over the aperture or a permeable cap fitted over the aperture. By diffusing and slowing the flow of fluid, the risk of damage to the interior of the eye is decreased and more fluid is maintained near the tip of the bore after being expelled from the aperture.

7 Claims, 4 Drawing Sheets

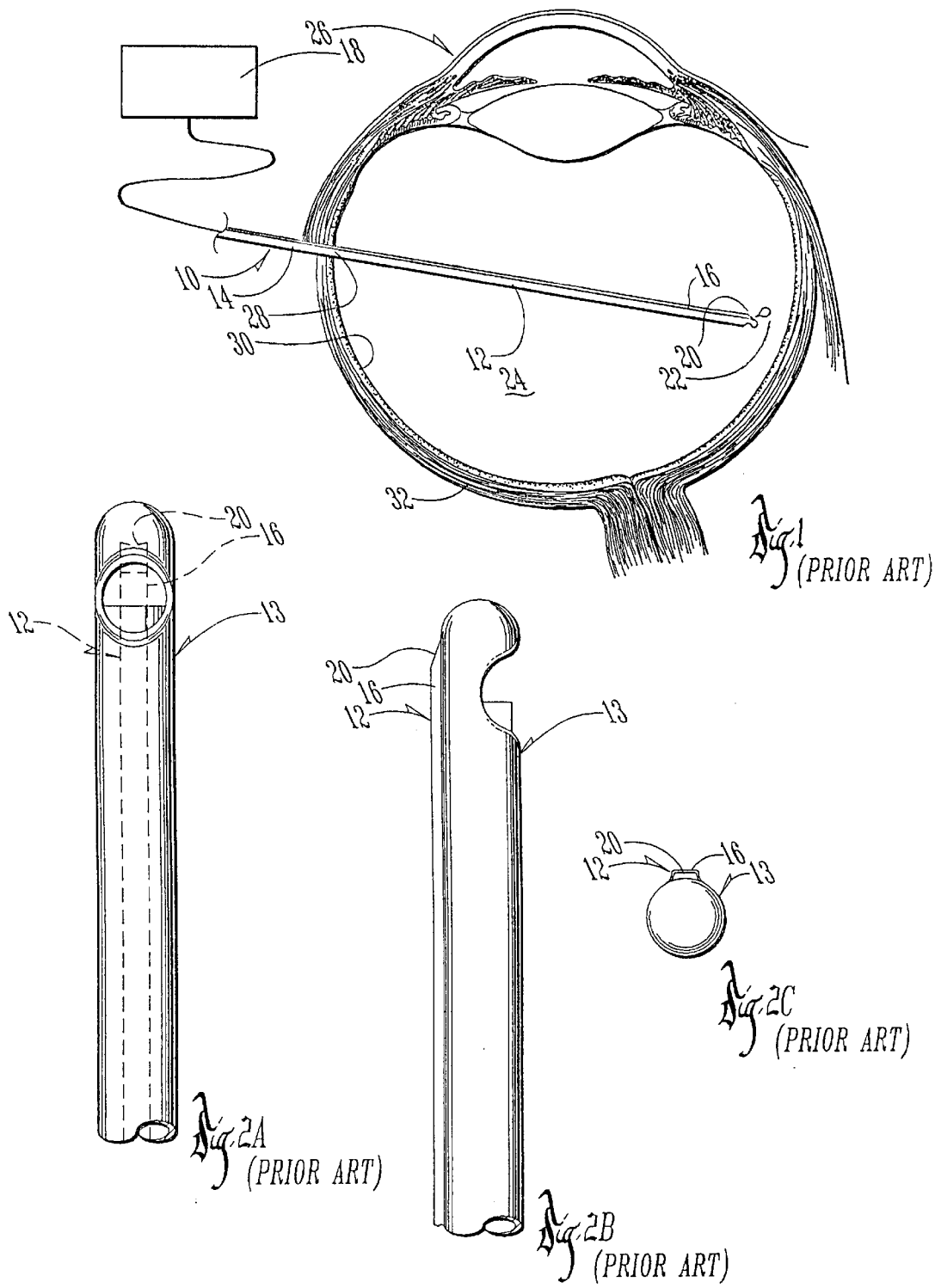

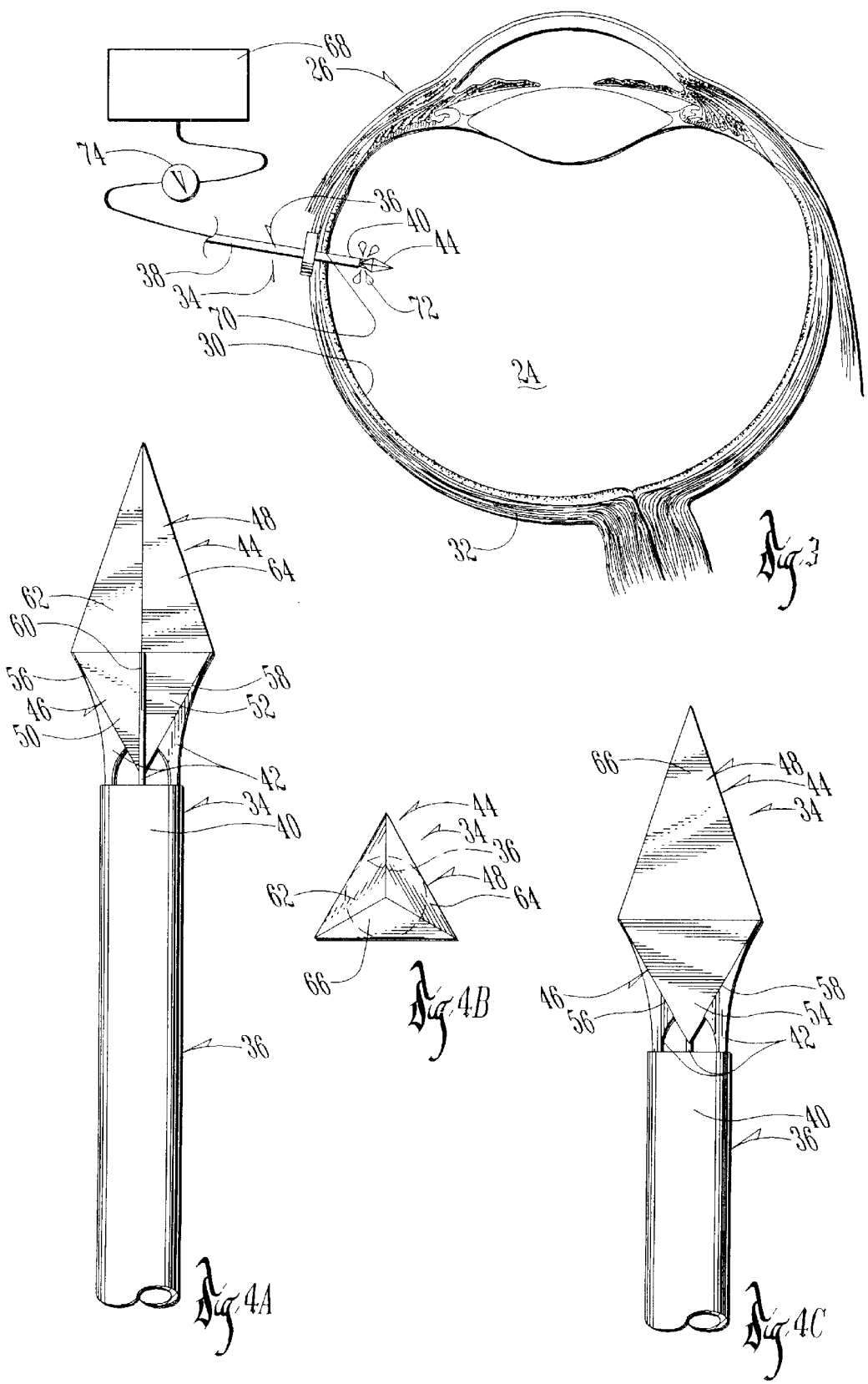

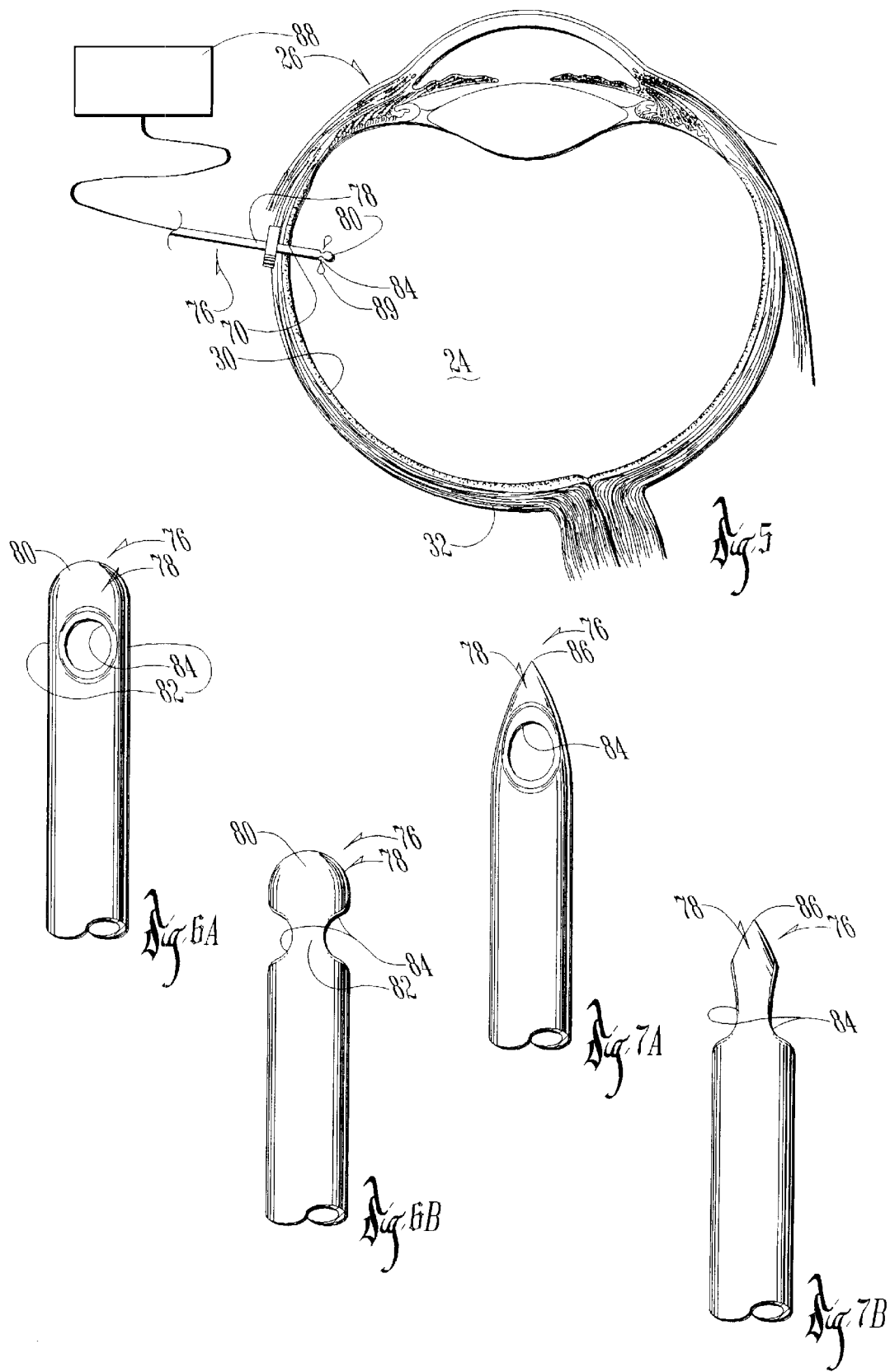

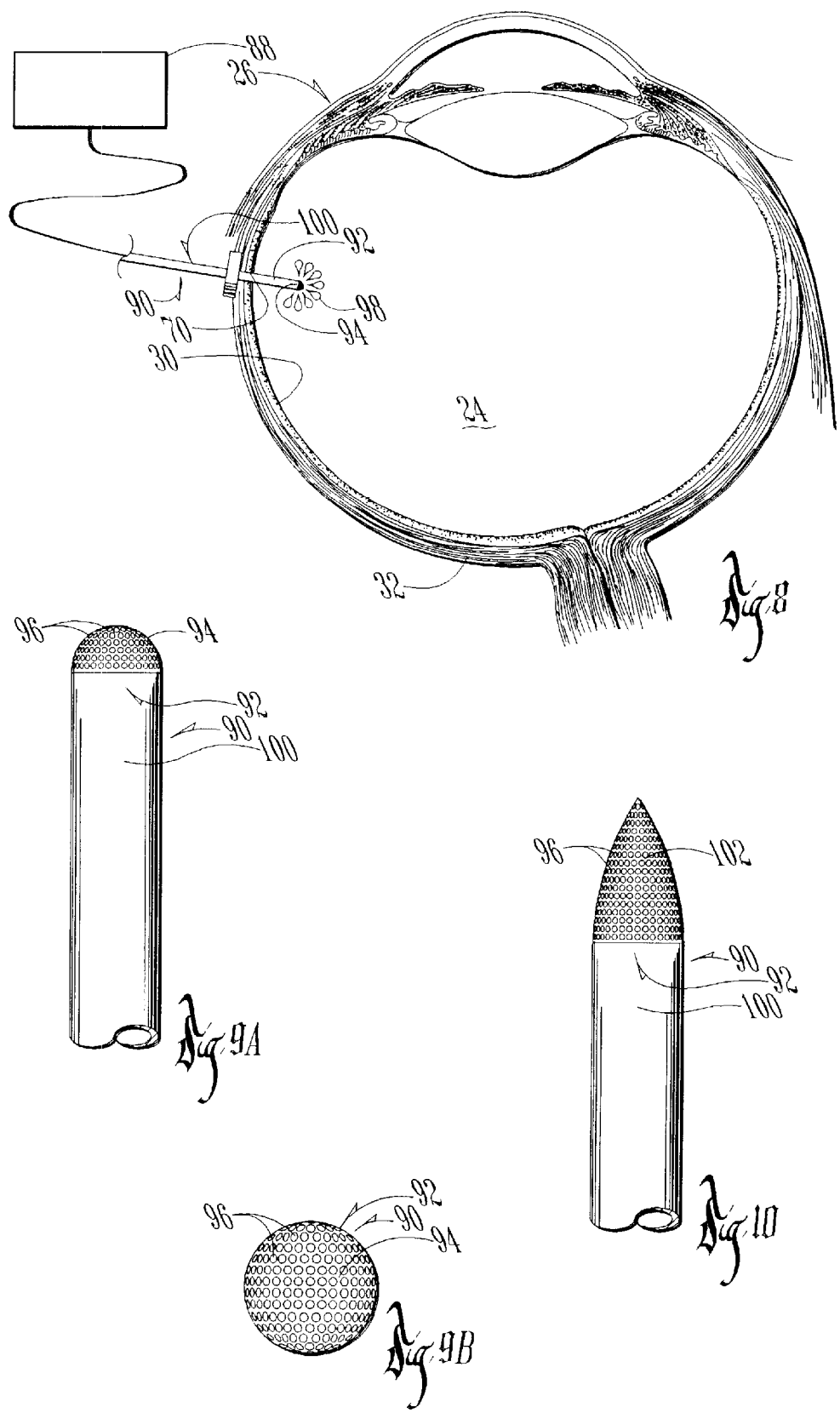

SURGICAL INFUSION TOOL WITH FLOW DIFFUSER

BACKGROUND OF THE INVENTION

1. Field of the Invention

The present invention relates to a surgical tool and, more particularly, to a surgical infusion tool having means for diffusing a fluid emanating from the tool.

2. Description of the Prior Art

Ophthalmologists use a wide variety of surgical tools to perform the different types of procedures associated with each individual medical condition of the eye. In a large number of procedures, including vitrectomy and retinal detachment surgery, it is often necessary to infuse a fluid, such as air, perfluoropropane ($C_3F_8$), or saline, into the vitreous cavity of the eye.

It is known in the art to infuse such fluid through a cannula which is inserted through a surgical incision and into the vitreous cavity of the eye. An irrigating solution such as a saline solution, or a gas such as air, is thereafter injected through the cannula into the vitreous cavity. In these prior art procedures, however, the cannula is provided with a single outlet. The drawback associated with such prior art cannulas is that the pressure, force and mass flux of the fluid exiting the cannula is concentrated by the relatively large single port. The pressure, force and mass flux exerted by the fluid exiting the cannula may cause damage to the retina or other sensitive portions of the inner eye.

It is also known in the art, as described in U.S. Pat. No. 5,547,473, issued to Peyman, to provide a multi-port tube which surrounds a vitrectomy probe. The drawback associated with this type of prior art device is the difficulty of infusing liquid, such as a saline solution, through the necessarily small ports of the device. An additional drawback associated with such a device is the relatively large diameter of the device in relationship to the relatively small amount of fluid capable of being infused through the small exterior gas delivery channel secured to the exterior of the vitrectomy cutter. This arrangement requires an incision much larger than the diameter of the fluid delivery tube. Accordingly, this type of device requires a very large incision to deliver a moderate amount of fluid to the eye.

The difficulties encountered hereinabove are sought to be eliminated by the present invention.

SUMMARY OF THE INVENTION

The present invention comprises a surgical tool for injecting a fluid into a patient. The tool is provided with a housing having a sidewall defining a longitudinal bore having a central axis. The sidewall is provided with an aperture and means are coupled to the housing for forcing the fluid through the central axis of the housing and out of the aperture. A flow diffuser is coupled to the housing and positioned over the aperture.

In the preferred embodiment, the diffuser comprises means for separating the aperture into a plurality of openings to diffuse fluid as it exits the aperture. The flow diffuser can separate the aperture into two or more openings, or may be a cone positioned over the aperture to divert the flow of fluid over the perimeter of the opening.

BRIEF DESCRIPTION OF THE DRAWINGS

FIG. 1 is a side view in partial cut-away showing the prior art cannula infusing fluid into the vitreous cavity of the eye;

FIG. 2a is a bottom elevation of the prior art cannula of FIG. 1;

FIG. 2b is a side elevation of the prior art cannula of FIG. 1;

FIG. 2c is a front elevation of the prior art cannula of FIG. 1;

FIG. 3 is a side elevation in partial cut-away showing the surgical tool of the present invention provided with a flow diffuser and infusing fluid into the vitreous cavity of the eye;

FIG. 4a is a bottom elevation of the surgical tool of FIG. 3;

FIG. 4b is a side elevation of the surgical tool of FIG. 4a;

FIG. 4c is a top elevation of the surgical tool of FIG. 4a;

FIG. 5 is a side elevation in partial cut-away showing an alternative embodiment of the present invention infusing fluid into the vitreous cavity of the eye;

FIG. 6a is a bottom elevation of the surgical tool of FIG. 5;

FIG. 6b is a side elevation of the surgical tool of FIG. 5;

FIG. 7a is a bottom elevation of an alternative embodiment of the surgical tool of FIG. 6a;

FIG. 7b is a side elevation of the alternative embodiment of the surgical tool of FIG. 7a;

FIG. 8 is a side elevation in partial cut-away of another alternative embodiment of the present invention infusing fluid into the vitreous cavity of the eye;

FIG. 9a is a bottom elevation of the surgical tool of FIG. 8;

FIG. 9b is a front elevation of the surgical tool of FIG. 8; and

FIG. 10 is a bottom elevation of an alternative embodiment of the surgical tool of FIG. 8.

DETAILED DESCRIPTION OF THE PREFERRED EMBODIMENT

With reference to the drawings, shown in FIG. 1 is a prior art surgical tool (10) having a longitudinal bore forming a fluid transfer housing (12) secured to a vitrectomy cutter (13). The housing (12) is provided with a proximal end (14) and a distal end (16). The tool (10) is coupled to a fluid supply (18) such as an air compressor, a syringe filled with saline solution, or any other fluid supply known in the art.

The distal end (16) of the housing (12) is provided with an opening (20) on the side to allow the distal end (16) of the housing (12) to act as a diffuser to allow fluid (22), such as air, to pass out of the opening (20) rather than the distal end (16) of the housing (12). As shown in FIG. 1, when it is desired to add fluid (22) to the vitreous cavity (24) of an eye (26), the surgical tool (10) is inserted through a sclerotomy incision (28) provided in the eye (26). The surgical tool (10) is inserted as deeply as required, and fluid (22) is then transferred from the fluid supply (18) through the housing (12) out of the opening (20) and into the vitreous cavity (24), using a control box (not shown), such as those known in the art, a syringe plunger (not shown), or similar fluid moving means.

As shown in FIGS. 2a, 2b and 2c, the housing (12) is provided with a single aperture (20). As can be seen in FIG. 1, fluid (22) leaves the housing (12) through this single aperture (20). This single aperture (20) causes the fluid (22) moving out of the housing (12) to leave the housing (12) at a relatively high pressure, force and mass flux. If, as shown in FIG. 1, the aperture (20) is positioned close to a sensitive portion of the eye (26), such as the retina (30), the pressure, force and mass flux exerted by the fluid, might injure the retina (30), or other delicate structures of the eye.

The present invention is designed to overcome these drawbacks associated with the prior art. Shown in FIG. 3 is an improved surgical tool (34), having a shaft (36). The shaft (36) is provided with a proximal end (38) and a distal end (40). As shown in FIG. 4a, soldered to the distal end (40) of the shaft (36) are three brackets (42). Soldered to the brackets (42) is a flow diffuser (44). The brackets (42) and flow diverter (44) are preferably constructed of solid surgical steel or similarly suitable material. As shown in FIGS. 4a–c, the flow diffuser (44) is provided with a lower pyramidal portion (46) and an upper pyramidal portion (48). As shown in FIGS. 4a and 4c, the lower pyramidal portion (46) is provided with three faces (50), (52) and (54), secured to one another at three corners, (56), (58) and (60). The brackets (42) are secured to the lower pyramidal portion (46) at the three corners (56), (58) and (60). The upper pyramidal portion (48) is also provided with three faces (62), (64) and (66) to allow for ease of insertion of the improved surgical tool (34) (FIGS. 3 and 4b). As shown in FIG. 3, the proximal end (38) of the shaft (36) is coupled to a fluid supply (68) such as an air compressor, a saline filled syringe, or other suitable fluid supply known in the art.

To operate the improved surgical tool (34) of the present invention, the distal end (40) of the improved surgical tool (34) is inserted into the vitreous cavity (24) though a sclerotomy incision (70). The distal end (40) of the improved surgical tool (34) is inserted into the vitreous cavity (24) to the desired position. Secured around the shaft (36) is a flange (71). The improved surgical tool (34) is temporarily fixated through the sclera by suturing the flange (71) to the external sclera as is known in the art of vitrectomy surgery. Pressure within the fluid supply (68) moves fluid (72) from the fluid supply (68) through the shaft (36) and out the distal end (40) of the improved surgical tool (34). The flow of fluid (72) from the fluid supply (68) to the distal end (40) may be controlled by a valve (74) such as those known in the art.

As can be seen in FIG. 3, as the fluid (72) exits the distal end (40) of the improved surgical tool (34), the flow diverter (44) diffuses the fluid (72) radially from the shaft (36). By diffusing the fluid (72) over a wide area, pressure, force and mass flux resulting from the infusion of fluid (72) into the vitreous cavity (24) are reduced and potential damage to the retina (30) and other sensitive areas of the eye (26) are also reduced. Additionally, by diffusing the fluid (72) slowly over a larger area, more fluid (72) remains in the area of the distal end (40) of the improved surgical tool (34).

Shown in FIG. 5 is an alternative surgical tool (76) having a distal end (78). As shown in FIGS. 6a–b, the distal end (78) of the surgical tool (76) is provided with a rounded tip (80). A portion of the housing (82) is positioned over one large aperture to form two smaller apertures (84) on either side of the housing (82). Alternatively, as shown in FIGS. 7a–b, the alternative surgical tool (76) may be provided with a pointed tip (86) to aid in insertion of a surgical tool (76) into the vitreous cavity (24) of the eye (26). As shown in FIG. 5, the alternative surgical tool (76) is provided with a fluid supply (88), such as that described above, to supply fluid (89) through the distal end (78) of the alternative surgical tool (76). By providing a pair of apertures (84), the pressure generated by the fluid (89) entering the vitreous cavity (24) of the eye (26) is cut in half, thereby reducing the potential for damage to the retina (30) and other portions of the eye (26).

Shown in FIG. 8 is a second alternative surgical tool (90) provided with a distal end (92). As shown in FIGS. 9a–b, the distal end (92) of the second alternative surgical tool (90) is provided with a rounded, perforated cap (94) constructed of thin surgical steel or similarly suitable material. The perforated cap (94) is preferably provided with a plurality of apertures (96) to evenly diffuse fluid (98) flowing out of the distal end (92) of the second alternative surgical tool (90). The perforated cap (94) may either be soldered or welded to a shaft (100) of the second alternative surgical tool (90), or may be an integral part of the shaft (100). As shown in FIG. 8, by diffusing the fluid (98) over the entire surface of the perforated cap (94), the force of the fluid (98) exiting the second alternative surgical tool (90) is greatly reduced, thereby reducing the potential for damage to the retina (30) of the eye (26). Alternatively, as shown in FIG. 10, the second alternative surgical tool (90) may be provided with a perforated conical cap (102) to aid in insertion of the tool (90) into the vitreous cavity (24) of the eye (26). (FIGS. 8 and 10).

Although the invention has been described with respect to a preferred embodiment thereof, it is to be understood that it is not to be so limited, since changes and modifications can be made therein which are within the full intended scope of this invention as defined by the appended claims. For example, it is anticipated that various gauges of housings may be used and that the device may be made in the form of a larger laproscopic tool for surgical uses in other parts of the body. It is additionally anticipated that various fluids may be infused into and removed from the body with the surgical tool of the present invention.

What is claimed is:

1. A surgical tool for injecting a fluid into a patient, the surgical tool comprising:
   a. a housing having a distal end and a sidewall defining a longitudinal bore smaller than fifteen (15) gauge in diameter, having a central axis, said sidewall being provided with an aperture substantially at said distal end of said housing;
   b. means coupled to said housing for forcing the fluid through said central axis of said housing and out of said aperture; and
   c. a flow diffuser coupled to said housing and positioned over said aperture.

2. The surgical tool of claim 1, wherein said flow diffuser is a permeable cap.

3. The surgical tool of claim 2, wherein said cap is rounded.

4. The surgical tool of claim 2, wherein said cap is conical.

5. The surgical tool of claim 2, wherein said permeable cap is provided with a plurality of holes.

6. The surgical tool of claim 1, wherein said aperture is in fluid communication with said central axis.

7. The surgical tool of claim 1, wherein said longitudinal bore is larger than thirty-two (32) gauge in diameter.

* * * * *